(12) United States Patent
Medas

(10) Patent No.: US 10,898,368 B2
(45) Date of Patent: Jan. 26, 2021

(54) ERGONOMIC MENSTRUAL CUP

(71) Applicant: TEOLAB, Neuilly-sur-Seine (FR)

(72) Inventor: Bertrand Medas, Lyons (FR)

(73) Assignee: TEOLAB, Neuilly-sur-Seine (FR)

( * ) Notice: Subject to any disclaimer, the term of this patent is extended or adjusted under 35 U.S.C. 154(b) by 315 days.

(21) Appl. No.: 15/746,695

(22) PCT Filed: Jul. 19, 2016

(86) PCT No.: PCT/FR2016/051845
§ 371 (c)(1),
(2) Date: Jan. 22, 2018

(87) PCT Pub. No.: WO2017/017340
PCT Pub. Date: Feb. 2, 2017

(65) Prior Publication Data
US 2018/0214298 A1   Aug. 2, 2018

(30) Foreign Application Priority Data
Jul. 24, 2015 (FR) ..................... 15 57046

(51) Int. Cl.
A61F 5/455 (2006.01)

(52) U.S. Cl.
CPC ............ *A61F 5/4553* (2013.01); *A61F 5/455* (2013.01)

(58) Field of Classification Search
CPC .... A61F 5/4553; A61F 13/2045; A61F 5/455; A61F 6/08; A61B 2010/0074; A61K 9/0036; Y10T 16/476; B25G 1/102; B26B 21/522
See application file for complete search history.

(56) References Cited

U.S. PATENT DOCUMENTS

| | | | | |
|---|---|---|---|---|
| 2,061,384 A | * | 11/1936 | Manegold | A61F 5/4553 604/330 |
| 2,616,426 A | | 11/1952 | Gordon | |
| 4,381,771 A | | 5/1983 | Gabbay | |
| 5,295,984 A | | 3/1994 | Contente et al. | |
| 6,471,186 B1 | * | 10/2002 | Lawless | B25C 11/00 254/25 |
| 8,795,248 B2 | | 8/2014 | Shihata | |

(Continued)

FOREIGN PATENT DOCUMENTS

| | | |
|---|---|---|
| DE | 202009008893 | 10/2009 |
| WO | 9843687 | 10/1998 |
| WO | 2006058409 | 6/2006 |

OTHER PUBLICATIONS

International Search Report issued in International Application No. PCT/FR2016/051845 dated Oct. 20, 2016 (7 pages).

(Continued)

*Primary Examiner* — Peter S Vasat
*Assistant Examiner* — Meagan Ngo
(74) *Attorney, Agent, or Firm* — Hamre, Schumann, Mueller & Larson, P.C.

(57) ABSTRACT

A menstrual cup (10) having a flared bottom portion (20), including a plurality of non-convex grip surfaces (22, 24) that are distributed in substantially axisymmetric manner at least on said flared bottom portion (20) and that are configured so as to be able to be pinched between the fingers in order to facilitate removal of the cup.

16 Claims, 2 Drawing Sheets

(56) References Cited

U.S. PATENT DOCUMENTS

| | | | |
|---|---|---|---|
| 2005/0044647 A1* | 3/2005 | Hohlbein | A46B 17/08 15/167.1 |
| 2008/0077097 A1* | 3/2008 | Chambers | A61F 5/4553 604/330 |
| 2008/0092337 A1* | 4/2008 | Gross | B25G 1/102 16/430 |
| 2008/0163463 A1* | 7/2008 | Hulden | B25G 1/105 16/430 |
| 2008/0200888 A1* | 8/2008 | Gooch | A61F 5/4553 604/330 |
| 2013/0061481 A1* | 3/2013 | Cooney | B26B 21/522 30/526 |
| 2013/0110060 A1 | 5/2013 | Shihata | |
| 2014/0012216 A1 | 1/2014 | Shaviv | |

OTHER PUBLICATIONS

Written Opinion issued in International Application No. PCT/FR2016/051845 dated Oct. 20, 2016 (4 pages).

Office Action issued for corresponding Colombian Patent Application No. NC2018/0000965, dated Mar. 29, 2019, 6 pages.

* cited by examiner

ERGONOMIC MENSTRUAL CUP

FIELD OF THE INVENTION

The invention relates to a menstrual cup. Such a cup is intended to be inserted into the vagina and be worn by a woman for the duration of menstruation so as to collect the menstrual flow.

With this aim, the cup is in the shape of a small cup with rounded edges, formed from resilient material.

Its opening in the top portion is usually defined by a sealing ring that ensures sealing of the cup when it is in place in the vagina. Below the ring, the cup is generally made up mainly of an upside down dome-shaped flared bottom portion, which is connected to the sealing ring either directly or else by means of a substantially cylindrical junction portion (referred to below as a 'cylindrical portion'). The flared bottom portion usually terminates at the bottom with a small stem serving to facilitate removal of the cup.

TECHNOLOGICAL BACKGROUND

The feminine hygiene market has changed considerably in recent years. Compared to tampons or sanitary pads, menstrual cups appear to be an increasingly suitable solution for modern women. Such a cup is disclosed for example in document U.S. Pat. No. 2,616,426.

However, the shapes of current cups leave much to be desired in terms of ease of insertion of the cup into the vagina and ease of removal therefrom.

Insertion of a menstrual cup is generally done by first folding the cup on itself. The cup is then put into place in the vagina, where it unfolds and returns to its initial shape.

The resilience of the material of the cup causes the outside surface of its sealing ring to be pressed against the vaginal wall, which allows the ring to be relatively leaktight. The menstrual flow may then be collected in the inside cavity of the cup.

In general, a menstrual cup terminates at the bottom with a small stem. Removal of the cup begins by taking hold of the cup by its stem. By pulling on that stem, the cup can initially be caused to move downwards towards the opening of the vagina, and then possibly removed from the vagina.

However, pulling on the stem to remove the cup creates a very unpleasant suction effect, with the edges of the cup pressing against the vaginal wall.

The object of the present invention is to overcome that difficulty and to provide a menstrual cup having a flared bottom portion that is of moderate cost, and that can be removed without giving rise to unpleasant sensations.

This object is achieved by the fact that the menstrual cup includes a plurality of non-convex grip surfaces that are distributed in substantially axisymmetric manner at least on said flared bottom portion and that are configured so as to be able to be pinched between the fingers in order to facilitate removal of the cup.

For ergonomic reasons, the menstrual cup of the invention preferably includes exactly either two grip surfaces, or three grip surfaces.

Preferably, the bottom portion has exactly two faces facing each other, configured so as to be able to be pinched between the thumb and the index finger.

As previously mentioned above, when a cup terminates in a stem, pulling on the stem in order to remove the cup is ineffectual and may even be painful.

By means of the invention, the cup may be removed without having to pull on the stem in that way.

In the event that a cup of the invention includes a stem, the stem should preferably serve only to guide the fingers towards the bottom portion of the cup, so that the fingers can be placed easily on the grip surfaces of the cup. It is possible to locate the grip faces of the cup easily with the fingers due to their non-convex shape.

In order to enable the cup to be removed from the vagina, it has been found, advantageously, that pressure exerted on the bottom portion of the cup makes it possible to free or separate the cup from the walls of the vagina, and thus enable it to be removed.

In particular, the grip surfaces may be used to turn the cup about its axis and thus unstick it (or at least separate it) from the walls of the vagina.

This is made possible by the grip surfaces, which offer grip for the fingers and make it possible to transmit a rotary torque (whereas conversely it is very difficult to turn a cup having a bottom portion that is in the form of a body of revolution).

Therefore, the cup is removed by pressing the bottom portion of the cup, and possibly by turning it; this/these operation(s) make(s) it possible to unstick the cup from the vaginal wall; the cup may then be removed easily by pinching the grip surfaces between the fingers and by pulling the cup out of the vagina.

The fact that the grip surfaces are non-convex, as described above, means that at least in one section plane, the section of these surfaces forms a curve that is non-convex: for example, a straight line segment, or a concave curve (depressed towards the inside of the cup).

In particular, the grip surfaces may therefore be substantially plane surfaces; trough-shaped surfaces (with the depression directed inwards); depressed surfaces (in particular, the depression being complementary to the shape of the fingers).

In an embodiment, the flared bottom portion of the cup is defined in part (and possibly for the most part) by a surface of revolution, and the grip surfaces are depressed relative to said surface of revolution.

In an embodiment, each of the grip surfaces is a profiled surface. The term "profiled surface" is used to designate a surface generated by moving a generator curve along a straight line, or in a given direction of movement.

The direction of movement may in particular be a direction that is perpendicular to the axis of the cup.

By way of example, in an embodiment, the bottom portion of the cup is defined in part by a surface of revolution, and the grip surfaces are profiled in a direction of movement that is substantially circumferential, in a section plane that is horizontal, relative to this surface of revolution.

In an embodiment, the profiled shape is of section that is substantially rectilinear section. The generator curve is thus substantially a straight line segment.

In an embodiment, in a plane perpendicular to an axis of the cup at mid-height of the grip surfaces, the sum of the angles at the vertex of the grip surfaces is greater than 900. The grip surfaces thus present a large surface area, which makes the cup easier to grip and which makes it possible in particular to turn the cup with the fingers more easily than if the grip surfaces were smaller.

In an embodiment, said grip surfaces are arranged at below 70%, and preferably below 50%, of the height of an inside cavity of the cup from a bottom of said cavity. Thus, the presence of the grip surfaces does not substantially reduce the capacity of the inside cavity of the cup.

In an embodiment, at least a portion of said grip surfaces presents a pattern and/or a grain.

The term "pattern" is used herein to designate a particular pattern in relief on the face or faces and that is suitable for being identified visually.

The term "grain" refers to a small pattern in relief that is suitable for being felt but that does not modify the general shape of the grip surface or surfaces.

The pattern and/or the grain makes it possible to distinguish the grip surfaces from the remainder of the bottom portion of the cup (from the portion of the bottom portion of the cup that is other than the grip surfaces); it being possible in particular for said remainder to be smooth or substantially smooth, at least in comparison with the portion of the grip surfaces that present the pattern or the grain.

Furthermore, another drawback mentioned by users who have tested a menstrual cup is its comfort in use, and in particular the presence of a prominent stem at the base of the cup.

Advantageously, in order to overcome that problem, in an embodiment of the invention the bottom portion of the cup does not have a stem. The absence of a stem is reflected in particular in the fact that the thickness of the cup at its low point is less than one-third of the maximum diameter of an inside cavity of the cup. Preferably, the thickness of the cup at its low point is even less than one-fifth of the maximum diameter of the inside cavity of the cup.

In known manner, the top of a menstrual cup is generally constituted by a sealing ring.

In an embodiment, the menstrual cup further includes at least one pressure-equalizing passage, arranged between the inside and the outside of the cup, said at least one passage opening out below the ring.

Thus, when the grip surfaces of the cup are pressed in order to remove it, advantageously the cup becomes unstuck from the vaginal wall at the outside orifice of at least one of said passages. Communication between the inside and the outside of the cup is therefore established by the passage: this communication immediately causes the pressures between the inside and the outside of the cup to be equalized, which makes the cup easier to remove by eliminating any sensation of suction.

Preferably, the outside orifice(s) of the pressure-equalizing passage(s) are arranged substantially in register with the grip surface(s). When a grip surface is pressed, the portion of the cup that is unstuck the most from the vaginal wall is the portion of the cup that is situated substantially in register with the grip surface (or grip surfaces) that has(have) been pressed.

Therefore it is most efficient to make the outside orifices of the pressure-equalizing passages of the cup in this portion of the outside surface of the cup.

Preferably, the outside orifice(s) of the pressure-equalizing passage(s) are situated just below the sealing ring, e.g. at a distance below the bottom edge of the ring that is less than half the outside radius of the ring.

In an embodiment, the sealing ring has an outer cylindrical surface over a height that is greater than $1/10^{th}$, and preferably greater than $1/5^{th}$, of an outside radius of the ring.

Thus, this outer cylindrical surface forms a large surface area intended for being in contact with the wall of the vagina, in contrast for example with an outside surface in the shape of an annulus, which would enable contact with the wall of the vagina only along a line. Consequently, such a ring confers to the cup particularly good sealing.

In an embodiment, the sealing ring has a top surface that slopes towards the inside of the cup, i.e. in the shape of a funnel. This embodiment facilitates entry of the menstrual flow into the cup and reduces the risk of some of the flow not being collected by the cup.

BRIEF DESCRIPTION OF THE DRAWINGS

The invention can be well understood and its advantages appear better on reading the detailed description given below of embodiments shown as non-limiting examples. The description refers to the accompanying drawings, in which.

DETAILED DESCRIPTION OF THE INVENTION

With reference to FIGS. 1 to 7, two menstrual cups 10 illustrating two embodiments of the invention are described below.

These two cups are identical with the exception of certain characteristics that are described below. Also, elements that are identical or similar in these two cups are given the same numerical references.

For elements shared by both shapes of cup, the following description is therefore shared by both shapes of cup.

Figure 6:
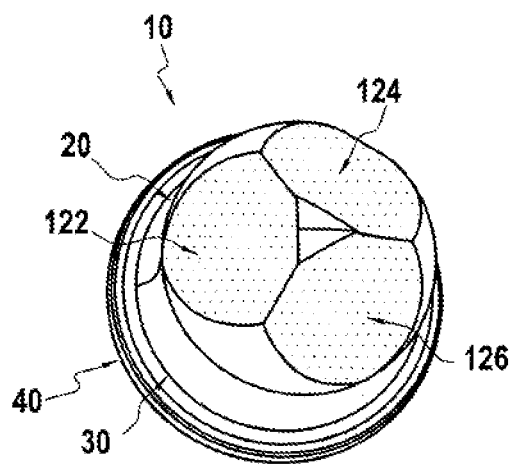
FIGS. 6 and 7 are diagrammatic views, respectively in perspective and in cross section, of a menstrual cup in a second embodiment of the invention.
Figure 7:
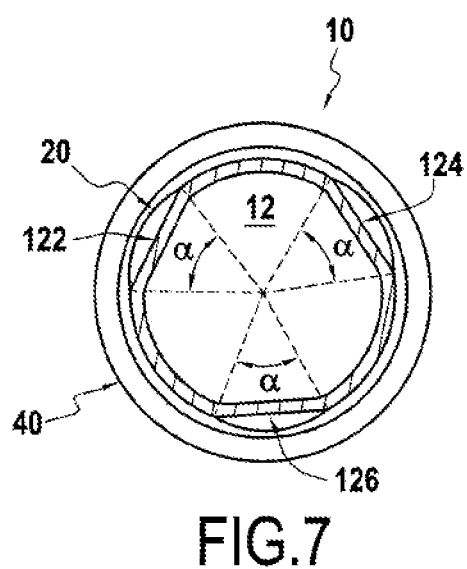

These two shapes are shown respectively by FIGS. 1 to 5 (first embodiment) and by FIGS. 6 and 7 (second embodiment).

The menstrual cup 10 presents a flared bottom portion 20, a cylindrical portion 30, and a sealing ring 40.

An inside cavity 12 is formed inside the cup 10.

The cup 10 is generally in the form of a body of revolution about an axis X. In order to simplify the description it is considered that the axis X is vertical and that the opening of the cavity 12 faces upwards.

The flared bottom portion 20 is the portion of the cup in which the diameter of the inside cavity 12 of the cup decreases.

In the first embodiment (FIGS. 1 to 5), the flared bottom portion 20 includes two profiled grip surfaces 22 and 24, that are axisymmetric and that are arranged facing each other.

In the second embodiment (FIGS. 6 and 7), the flared bottom portion includes three profiled grip surfaces 122, 124, and 126, that are axisymmetric and that are arranged facing each other.

The grip surfaces (22, 24; 122, 124, 126) are profiled surfaces.

In the embodiments shown, the grip surfaces are profiled surfaces with a cross-section that is substantially rectilinear.

Figure 1:
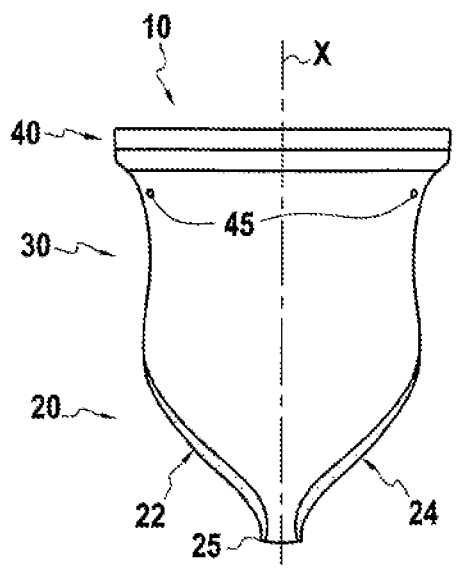
FIGS. 1 and 2 are two diagrammatic views, respectively from the front and from the side showing a menstrual cup in a first embodiment of the invention.
Figure 2:
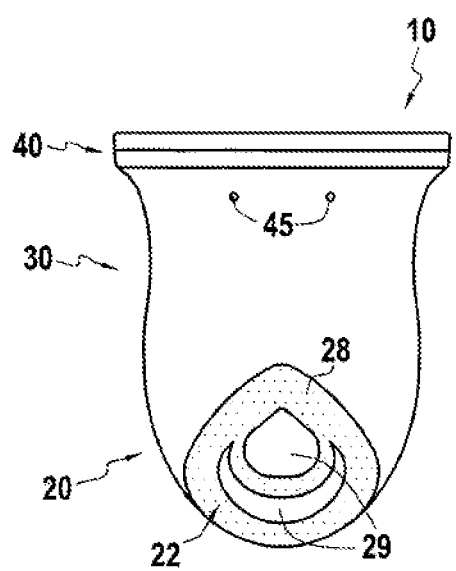
Figure 3:
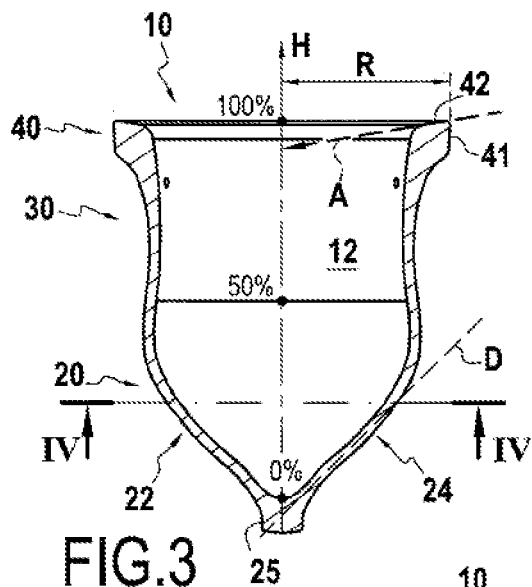
FIGS. 3 and 4 are section views of the menstrual cup of FIGS. 1 and 2, respectively in a meridian plane and in a transverse plane.

Thus, in the first embodiment, the grip surfaces 22, 24 are generated by moving a curve that forms substantially a straight line segment in a direction perpendicular to the section plane of FIG. 3. FIG. 3 shows the straight line D that can be considered as the straight line of which the segment for the surface 24 forms a part.

In the embodiments shown, the grip surfaces of the cup 10 are arranged on the bottom portion 20 only. They could possibly extend over the cylindrical portion 30.

These grip surfaces extend in particular only up to a height that is less than 50% of the height H of the inside cavity 12 of the cup. This height H is measured from the bottom of the cup, and has a value of 0% at the bottom of this cavity, and 100% at the top opening of the cavity (FIG. 3).

The grip surfaces occupy a relatively large area in the bottom portion 20, so as to engage the fingers and enable the cup to be gripped.

Figure 4:
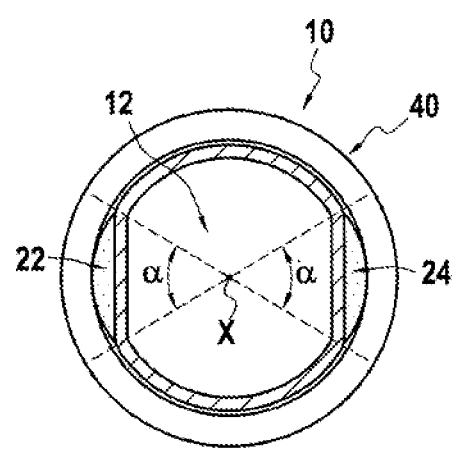
Figure 5:
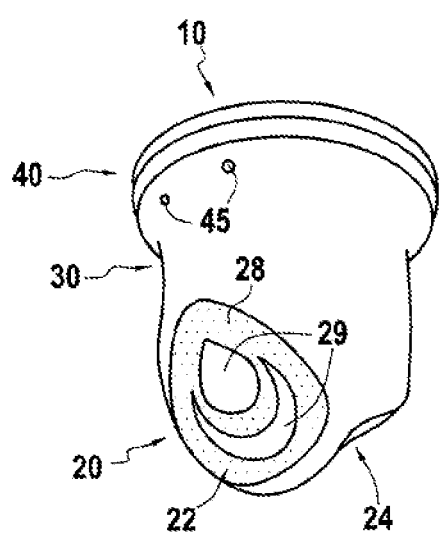
FIG. 5 is a diagrammatic perspective view of the menstrual cup of FIGS. 1 and 2.

Thus, as seen in FIG. 4 or 7, in a section of the cup in a transverse plane at mid-height of the grip surfaces, the sum of the angles at the vertex a of the grip surfaces is greater than 900.

The grip surfaces present visual and tactile aspects that are different from the rest of the outside surface of the bottom portion 20.

Thus, in the first embodiment, the grip surfaces 22 and 24 present a grain on grainy surfaces 28. This grain is obtained in conventional manner by using grainy surfaces of complementary shape that are provided in the mold for producing the cup 10.

The grip surfaces 22 and 24 are grainy over the entire surfaces 28, with the exception of gaps 29. These gaps 29 are the portions of the grip surface 22 and 24 that are not grainy, unlike the rest of the surfaces 22 and 24 that constitute the grainy surfaces 28. The gaps 29 therefore remain smooth like the rest of the outside surface of the cup 10.

The alternation of grainy surfaces and of smooth surfaces (surfaces 28/29) forms a pattern that makes it possible to recognize the grip surfaces 22 and 24 by touch and/or visually.

In the second embodiment, the grip surfaces 122, 124, 126 are entirely grainy and do not include any smooth gaps.

Advantageously, the presence of grip surfaces in the bottom portion of the cup 10 makes the stem completely pointless.

In the first embodiment, the bottom of the cup 10 includes just a small tip 25, in the shape of a ridge. This makes it possible to locate the end of the cup and makes it easier to place the fingers on the grip surfaces.

The top portion of the cup 10, in the vicinity of the sealing ring 40, includes pressure-equalizing passages 45. These passages present outer orifices (also given reference 45) that are generally situated in register with the grip surfaces 22, 24 (as can be seen in particular in FIG. 2). These passages are passages that pass through the wall of the cup and that therefore connect the inside cavity 12 of the cup to the outside thereof.

The sealing ring presents an outer cylindrical surface 41. This surface extends vertically (along the axis X) over a certain height. This height is greater than $1/10^{th}$ of the outside radius R of the ring 40 (FIG. 3).

The outer cylindrical surface 41 is intended to improve sealing by increasing the contact surface area between the upper outer edge of the cup and the wall of the vagina; and maintain sufficient stiffness, both during folding and during use of the cup once it is in place.

The ring 40 further presents a top surface 42 that slopes towards the inside of the cup. The shape of this surface 42 is indicated by arrow A in FIG. 3. The top surface 42 therefore presents a slope going down towards the inside of the cup, from the ridge formed at the top end of the cylindrical surface 41, to the junction between the ring 40 and the inside cavity 12 of the cup.

By means of the (radially) inward slope of this surface, menstrual flow located on this top surface of the ring 40 flows inside and not outside the cavity 12 of the cup.

Figure 8:
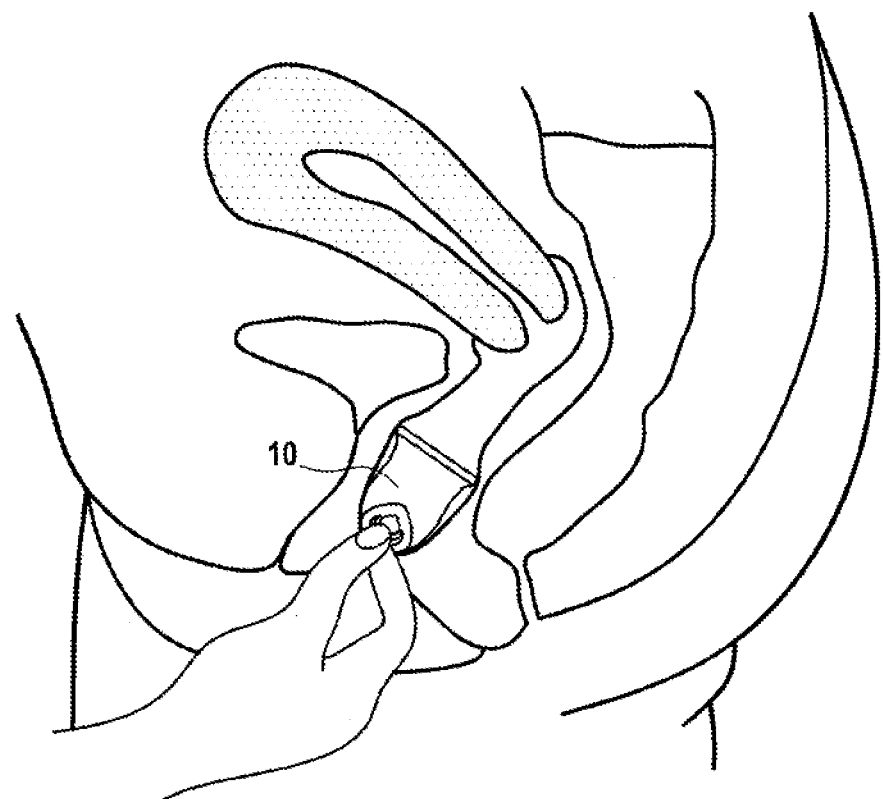
FIG. 8 is a section view showing the removal of a menstrual cup.

FIG. 8 is a diagram showing a cup 10 removal operation.

In order to remove said cup, it is necessary to pinch the bottom portion of the cup between the fingers. The cup 10 may be turned about its axis in order to separate it from the vagina; the cup is then pulled downwards and is thus extracted from the vagina.

Although the present invention is described with reference to specific embodiment examples, it is clear that various modifications and changes can be made to these embodiments without going beyond the general ambit of the invention as defined by the claims. Furthermore, individual characteristics of the various embodiments mentioned may be combined in additional embodiments. Consequently, the description and the drawings should be considered in a sense that is illustrative rather than restrictive.

The invention claimed is:

1. A menstrual cup having a flared bottom portion, the menstrual cup including a plurality of non-convex grip surfaces that are distributed in substantially axisymmetric manner at least on said flared bottom portion and that are configured so as to be able to be pinched between fingers in order to facilitate removal of the cup; and a sealing ring situated at a top of the menstrual cup, said sealing ring having an outer cylindrical surface, said sealing ring having a top surface that slopes going down towards an inside of the menstrual cup, from a ridge formed at a top end of the outer cylindrical surface to a junction between the sealing ring and an inside cavity of the menstrual cup.

2. The menstrual cup according to claim 1, wherein each of said grip surfaces is a profiled surface.

3. The menstrual cup according to claim 1, wherein, in a plane perpendicular to an axis of the cup at mid-height of the grip surfaces, a sum of angles at a vertex of the grip surfaces is greater than 90°.

4. The menstrual cup according to claim 1, wherein said grip surfaces are arranged at below 70% of a height of the inside cavity of the menstrual cup from a bottom of said cavity.

5. The menstrual cup according to claim 1, wherein at least a portion of said grip surfaces presents a pattern and/or a grain.

6. The menstrual cup according to claim 1, wherein the bottom portion does not have a stem.

7. The menstrual cup according to claim 1, further including at least one pressure-equalizing passage made between an outside and the inside of the menstrual cup, said at least one passage opening out below the sealing ring.

8. The menstrual cup according to claim 1, wherein the outer cylindrical surface extends over a height that is greater than $1/10^{th}$ of an outside radius of the sealing ring.

9. The menstrual cup according to claim 1, including exactly either two of the grip surfaces or three of the grip surfaces.

10. The menstrual cup according to claim 1, wherein said grip surfaces are arranged at below 50% of a height of the inside cavity of the menstrual cup from a bottom of said inside cavity.

11. The menstrual cup according to claim 1, wherein the outer cylindrical surface extends over a height that is greater than $1/5^{th}$ of an outside radius of the sealing ring.

12. The menstrual cup according to claim 1, wherein the flared bottom portion of the menstrual cup is not cylindrical.

13. The menstrual cup according to claim 1, wherein the flared bottom portion includes a tip in the shape of a ridge.

14. The menstrual cup according to claim 1, wherein the non-convex grip surfaces are substantially plane surfaces.

15. The menstrual cup according to claim 1, wherein the top surface slopes in a straight line going down towards the inside cavity of the menstrual cup.

16. The menstrual cup according to claim 1, wherein the menstrual cup includes exactly two of the non-convex grip surfaces, the two non-convex grip surfaces face each other at least on said flared bottom portion and the two non-convex grip surfaces are configured so as to be able to be pinched between a thumb and an index finger in order to facilitate removal of the menstrual cup.

\* \* \* \* \*